(12) United States Patent
Williams

(10) Patent No.: US 8,153,973 B2
(45) Date of Patent: Apr. 10, 2012

(54) METHOD FOR ANALYZING, LABELING AND CERTIFYING LOW RADIOCARBON FOOD PRODUCTS

(75) Inventor: Christopher P. Williams, Brunswick, OH (US)

(73) Assignee: Radiocarb Genetics, Inc., Akron, OH (US)

( * ) Notice: Subject to any disclaimer, the term of this patent is extended or adjusted under 35 U.S.C. 154(b) by 418 days.

(21) Appl. No.: 12/434,122

(22) Filed: May 1, 2009

(65) Prior Publication Data

US 2009/0282004 A1 Nov. 12, 2009

Related U.S. Application Data

(60) Provisional application No. 61/126,613, filed on May 6, 2008.

(51) Int. Cl.
*G01J 1/00* (2006.01)
(52) U.S. Cl. .................................................. 250/336.1
(58) Field of Classification Search ............... 250/336.1, 250/336.2
See application file for complete search history.

(56) References Cited

U.S. PATENT DOCUMENTS

| | | | | |
|---|---|---|---|---|
| 4,929,832 A | * | 5/1990 | Ledley | 250/328 |
| 5,478,990 A | * | 12/1995 | Montanari et al. | 235/375 |
| 2005/0064079 A1 | * | 3/2005 | Allen et al. | 426/549 |
| 2005/0075900 A1 | * | 4/2005 | Arguimbau | 705/1 |
| 2007/0275139 A1 | * | 11/2007 | Joerger et al. | 426/321 |

OTHER PUBLICATIONS

Ingalls et al., "Ten years of compound-specific radiocarbon analysis," 2005, Oceanography, vol. 18, No. 3, pp. 19-31.*

* cited by examiner

*Primary Examiner* — Kiho Kim
(74) *Attorney, Agent, or Firm* — Lerner, David, Littenberg, Krumholz & Mentlik, LLP

(57) ABSTRACT

Methods, particularly computer-implemented methods, are provided for analyzing, labeling, reporting, and certifying the radiocarbon abundance levels of low radiocarbon food products, including relevant chemical components of final products as well as components of lots used in manufacturing, so that manufacturers, consumers or other users of these products can have high confidence in their stated radiocarbon content and a better understanding of their potential effectiveness in reducing genetic damage. Other embodiments employ an algorithm to calculate an overall value or grade or range indicative of the product's known or estimated ability to either reduce the radiocarbon level of, or to reduce genetic damage occurring in, newly formed chromosomal material in consumers of such products, the chromosomal material comprising DNA and histone proteins and remote access by consumers to the computer-implemented methods, for example, via the Internet.

10 Claims, 6 Drawing Sheets

| A | B | C | D | E | F | G |
|---|---|---|---|---|---|---|
| Chromosomal Component | Residues | Carbons per Residue | Total No. Carbons | Relative Response Factor | Effective No. of Carbons | Effective % of Carbons |
| DNA Nucleotides | | | | | | (54.21%) |
| Adenosine | 118 | 10 | 1180 | 1.00 | 1180.0 | 15.70% |
| Thymidine | 118 | 10 | 1180 | 1.00 | 1180.0 | 15.70% |
| Cytidine | 82 | 9 | 738 | 1.10 | 811.8 | 10.80% |
| Guanosine | 82 | 10 | 820 | 1.10 | 902.0 | 12.00% |
| Histone Amino Acids | | | | | | (45.79%) |
| Lys | 171 | 6 | 1026 | 0.60 | 615.6 | 8.19% |
| Arg | 110 | 6 | 660 | 0.60 | 396.0 | 5.27% |
| Leu | 94 | 6 | 564 | 0.60 | 338.4 | 4.50% |
| Ala | 150 | 3 | 450 | 0.60 | 270.0 | 3.59% |
| Val | 78 | 5 | 390 | 0.60 | 234.0 | 3.11% |
| Ile | 53 | 6 | 318 | 0.60 | 190.8 | 2.54% |
| Thr | 74 | 4 | 296 | 0.60 | 177.6 | 2.36% |
| Glu | 56 | 5 | 280 | 0.60 | 168.0 | 2.24% |
| Tyr | 31 | 9 | 279 | 0.60 | 167.4 | 2.23% |
| Pro | 55 | 5 | 275 | 0.60 | 165.0 | 2.20% |
| Ser | 75 | 3 | 225 | 0.60 | 135.0 | 1.80% |
| Gly | 103 | 2 | 206 | 0.60 | 123.6 | 1.64% |
| Gln | 38 | 5 | 190 | 0.60 | 114.0 | 1.52% |
| Phe | 19 | 9 | 171 | 0.60 | 102.6 | 1.37% |
| His | 22 | 6 | 132 | 0.60 | 79.2 | 1.05% |
| Asn | 28 | 4 | 112 | 0.60 | 67.2 | 0.89% |
| Asp | 25 | 4 | 100 | 0.60 | 60.0 | 0.80% |
| Met | 10 | 5 | 50 | 0.60 | 30.0 | 0.40% |
| Cys | 4 | 3 | 12 | 0.60 | 7.2 | 0.10% |
| Trp | 0 | 11 | 0 | 0.60 | 0.0 | 0.00% |
| TOTAL | | | 9654 | | 7515.4 | 100.00% |

Fig. 2

| A | B | C | D | E | F | G | H |
|---|---|---|---|---|---|---|---|
| Chromosomal Component | Effective % of Carbons in the Chromosome | Radiocarbon Reduction in Low Radiocarbon Food | Amt of Low Radiocarbon Food (mg) | Amt of Normal Radiocarbon Food (mg) | Total Amount of Food (mg) | Amt of Low Radiocarbon Food as % of Total Food | Overall Effective Radiocarbon Reduction in the Chromosome |
| DNA Nucleotides | | | | | | | |
| Adenosine | 15.70% | 96.00% | 520 | 120 | 640 | 81.25% | 12.25% |
| Thymidine | 15.70% | 96.00% | 520 | 120 | 640 | 81.25% | 12.25% |
| Cytidine | 10.80% | 97.00% | 370 | 80 | 450 | 82.22% | 8.62% |
| Guanosine | 12.00% | 97.00% | 370 | 80 | 450 | 82.22% | 9.57% |
| Histone Amino Acids | | | | | | | |
| Lys* | 8.19% | 98.10% | 900 | 180 | 1080 | 83.33% | 6.70% |
| Arg | 5.27% | 96.50% | 780 | 170 | 950 | 82.11% | 4.17% |
| Leu* | 4.50% | 96.00% | 650 | 210 | 860 | 75.58% | 3.27% |
| Ala | 3.59% | 96.20% | 480 | 200 | 680 | 70.59% | 2.44% |
| Val* | 3.11% | 95.80% | 420 | 200 | 620 | 67.74% | 2.02% |
| Ile* | 2.54% | 96.00% | 360 | 140 | 500 | 72.00% | 1.75% |
| Thr* | 2.36% | 96.30% | 330 | 160 | 490 | 67.35% | 1.53% |
| Glu | 2.24% | 95.20% | 350 | 220 | 570 | 61.40% | 1.31% |
| Tyr** | 2.23% | 93.50% | 240 | 200 | 440 | 54.55% | 1.14% |
| Pro | 2.20% | 96.00% | 240 | 200 | 440 | 54.55% | 1.15% |
| Ser | 1.80% | 96.00% | 150 | 200 | 350 | 42.86% | 0.74% |
| Gly | 1.64% | 96.10% | 150 | 200 | 350 | 42.86% | 0.68% |
| Gln | 1.52% | 96.00% | 300 | 200 | 500 | 60.00% | 0.87% |
| Phe** | 1.37% | 93.00% | 150 | 200 | 350 | 42.86% | 0.54% |
| His* | 1.05% | 93.80% | 120 | 180 | 300 | 40.00% | 0.40% |
| Asn | 0.89% | 96.00% | 150 | 200 | 350 | 42.86% | 0.37% |
| Asp | 0.80% | 96.30% | 150 | 240 | 390 | 38.46% | 0.30% |
| Met** | 0.40% | 80.00% | 120 | 130 | 250 | 48.00% | 0.15% |
| Cys** | -0.10% | 96.00% | 40 | 120 | 160 | 25.00% | 0.02% |
| Trp* | 0.00% | 10.00% | 20 | 60 | 80 | 25.00% | 0.00% |
| TOTAL | 100.00% | - | 7880 | 4010 | 11890 | - | 72.23% |

Fig. 3

Low Radiocarbon Infant Formula ← 402

Product ID: LRIF-123456     Lot: 7890-AB-99 ← 403

← 404

|  | Amount present in one serving | Radiocarbon level (Reduction from natural background levels) |
|---|---|---|
| Nucleic Acids | 400 mg |  |
| Adenosine | 118 mg | 96% |
| Guanosine | 82 mg | 95% |
| Cytidine | 82 mg | 94% |
| Thymidine | 118 mg | 96% |
| Amino Acids | 2.0 g |  |
| Lys | 300 mg | 96% |
| Arg | 260 mg | 95% |
| Leu | 200 mg | 94% |
| Ala | 160 mg | 93% |
| Val | 140 mg | 95% |
| Ile | 120 mg | 95% |
| Thr | 110 mg | 94% |
| Glu | 80 mg | 96% |
| Tyr | 80 mg | 95% |
| Pro | 80 mg | 95% |
| Ser | 50 mg | 94% |
| Gly | 50 mg | 96% |
| Gln | 50 mg | 95% |
| Phe | 50 mg | 95% |
| His | 50 mg | 90% |
| Asn | 50 mg | 81% |
| Asp | 50 mg | 80% |
| Met | 40 mg | 69% |
| Cys | 40 mg | 72% |
| Trp | 40 mg | 5% |

405

Estimated Overall Effectiveness in Reducing Chromosomal Damage in Newly Formed Cells from Radiocarbon ← 406

For an infant (approx 22 lbs, or 10 kg) receiving two servings of this formula per day together with two servings of other ordinary infant formula – *47% Effective in Reducing Chromosomal Damage*

For an infant (approx 22 lbs, or 10 kg) receiving three servings of this formula per day together with one serving of other ordinary infant formula – *71% Effective in Reducing Chromosomal Damage*

For other situations involving different serving amounts, infants of different weight, or different ← 407
diets, visit our web site to use our free interactive program, *Estimates of Effectiveness in Reducing Chromosomal Damage from Radiocarbon*.

METHOD FOR ANALYZING, LABELING AND CERTIFYING LOW RADIOCARBON FOOD PRODUCTS

CROSS-REFERENCE TO RELATED APPLICATIONS

This application claims the benefit of the filing date of U.S. Provisional Patent Application No. 61/126,613 filed May 6, 2008, the disclosure of which is hereby incorporated herein by reference.

BACKGROUND

The invention relates to methods for analyzing, labeling and reporting the radiocarbon levels of food products produced for the purpose of reducing human genetic damage, and the certification of such methods.

Methods have been described (Matthews, U.S. Pat. No. 5,471,785; Miekka, U.S. Pat. No. 5,956,896; Williams, including U.S. Patent Publication 2007-0104761 and PCT Application No. PCT/US07/10775 filed May 3, 2007 (WO 2008/136793, published Nov. 13, 2008), each incorporated herein by reference) for producing low radiocarbon plants, animals, nutritional supplements, and related food products suitable for human nutrition. However, no detailed methods have been provided for analyzing, labeling, reporting, or certifying the radiocarbon levels of these products in ways that are both useful to and trusted by consumers, particularly when such products are intended specifically for use in reducing chromosomal damage and consequent health risks.

SUMMARY OF THE INVENTION

In one embodiment there is provided a method to analyze and report the radiocarbon content of a food product lot, comprising the steps: a) marking a product lot with an appropriate product lot identifier; b) taking one or more samples from said product lot; c) marking each of said samples with an appropriate sample identifier; d) analyzing said samples to measure the radiocarbon content of at least one carbon-containing component of one or more samples or mixture of samples from the same product lot; e) labeling the product lot with the results of the radiocarbon analysis done on its samples or otherwise providing a reporting mechanism to link the product lot identifier to the results of the radiocarbon analysis of its samples.

In another embodiment, the carbon-containing component in step (d) recited above comprises one or more members selected from the group consisting of (A) protein or amino acids; (B) DNA, RNA, nucleotides, nucleosides, purines, pyrimidines, or other nucleic acids; or (C) mixtures of (A) and (B).

In still another embodiment, the method employs an algorithm to calculate an overall value or grade or range indicative of the product's known or estimated ability to either reduce the radiocarbon level of, or to reduce genetic damage occurring in, newly formed chromosomal material in consumers of said product, said chromosomal material comprising DNA and histone proteins.

A further embodiment is directed to a computer-implemented method for providing personalized food radiocarbon information for a consumer of a food product, the food product having associated therewith product lot identification (ID) information corresponding to a lot from which the food product originated, the method comprising: (a) inputting to a computer system: (i) the lot ID information from a food product which the user has acquired; and (ii) personal consumer information comprising one or more personal characteristics of the consumer of the food product; and (b) the computer system calculating personalized food radiocarbon information for the consumer based on the inputted lot ID information and personal consumer information and based on preexisting radiocarbon information associated with the lot ID information of the food product; and (c) delivering to the consumer the information calculated in step (b).

The invention is also directed to a computer-implemented method for providing personalized food radiocarbon information for a consumer of a food product, the food product having associated therewith product identification (ID) information and lot ID information corresponding to a lot from which the food product originated, the method comprising: (a) inputting to a computer system: (i) the product ID information and lot ID information from a food product which the user has acquired; and (ii) personal consumer information comprising one or more personal characteristics of the consumer of the food product; and (b) the computer system calculating personalized food radiocarbon information for the consumer based on the inputted product ID information, lot ID information and personal consumer information and based on preexisting radiocarbon information associated with the lot ID information of the food product.

In a specific embodiment the invention is directed to a method for providing personalized food radiocarbon information for a consumer of a food product, comprising: (a) providing a plurality of lots of food products; (b) determining radiocarbon information about samples of food products from the lots; (c) associating the radiocarbon content of the samples from each lot with a lot ID; (d) labeling food products with the lot ID corresponding to the lot from which the food product originates; (e) providing a computer system for: (i) allowing user input of the lot ID of a food product the user has acquired and personal consumer information comprising one or more personal characteristics of the consumer of the food product; and (ii) calculating personalized food radiocarbon information for the consumer based on the personal consumer information and the radiocarbon content associated with the lot ID of the food product.

BRIEF DESCRIPTION OF THE DRAWINGS

FIG. 2 illustrates a calculation spreadsheet used to determine the effective percentage of carbons each nucleotide and amino acid contributes to human histones.

FIG. 3 illustrates a calculation spreadsheet used to determine the estimated effective percentage of radiocarbon reduction provided by a low radiocarbon food also eaten with ordinary food.

FIG. 4 illustrates a product label from an embodiment of the present invention.

DETAILED DESCRIPTION

Figure 1:
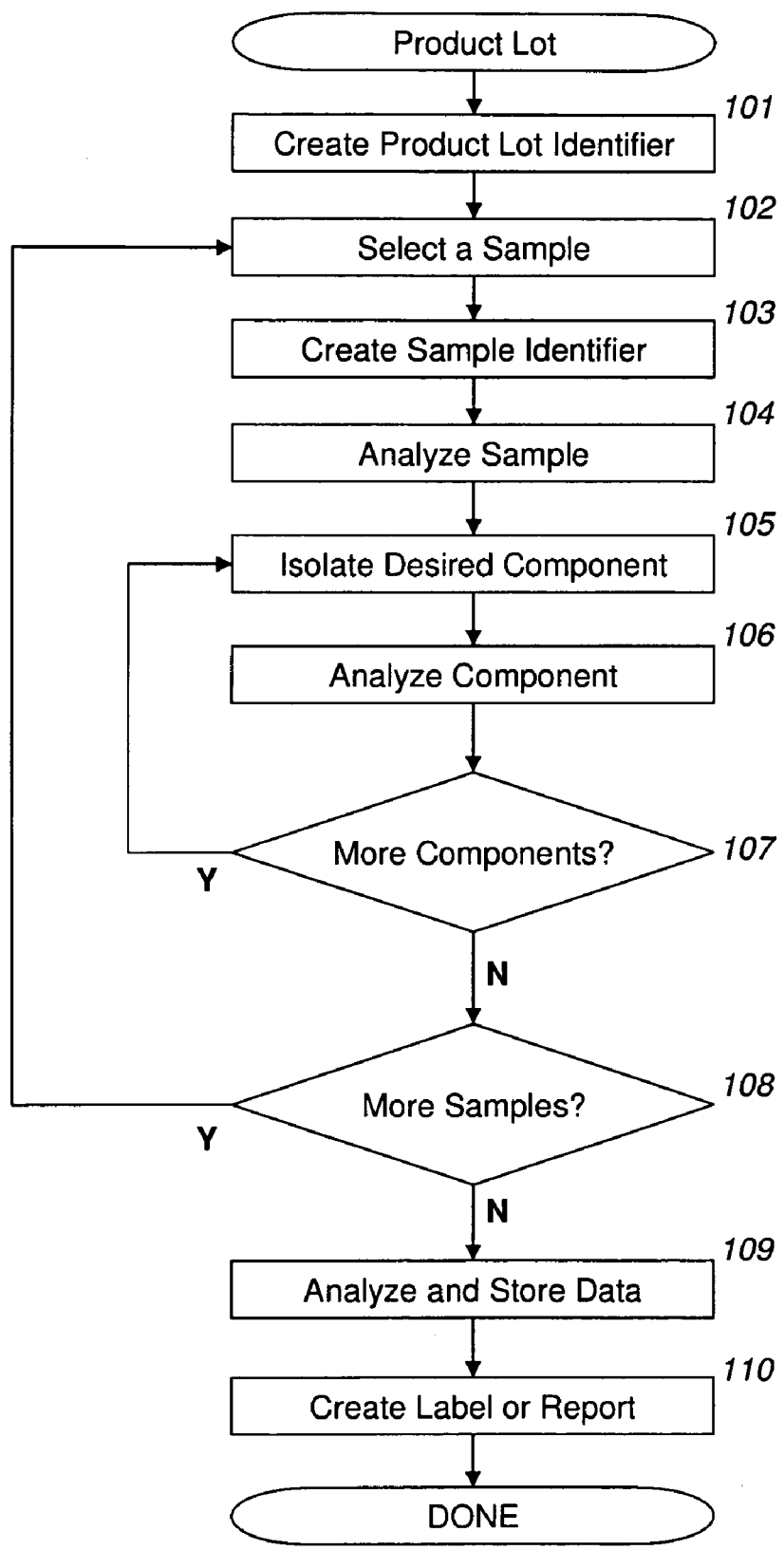
FIG. 1 is a flow diagram of the product and sample labeling and analysis process used in one embodiment of the present invention.

Establishing and maintaining a high degree of consumer confidence is essential when the property or characteristic which determines the product's value is difficult to determine or cannot be directly measured or confirmed by the average consumer. Such is the case of food products with reduced levels of radiocarbon. Because such products appear to be identical in terms of chemical and physical properties to ordinary food products with natural background levels of radiocarbon, the average consumer has no easy way of independently verifying the actual radiocarbon level of a given product or making the best use of it.

Furthermore, if a complex product consists of numerous components, in particular chemically distinct components, each of which may each vary in amount and in the level of radiocarbon, it is difficult for potential users to evaluate the suitability of that product for a particular use, or to compare two or more such complex products to decide which will be most effective for a particular use. Such is the case for food products or nutritional supplements which may vary considerably in their protein, DNA, amino acid or nucleotide content as well as in the radiocarbon level of each of these components. Consumers need some way to know which product will be most effective for them in reducing chromosomal damage and thus provide the greatest potential health benefits.

As an example, consider two different nutritional supplements containing amino acids which both claim to reduce chromosomal radiocarbon levels. One contains 1 g each of lysine and arginine which are both 95% reduced in radiocarbon, and the second contains 1 g each of phenylalanine, methionine, aspartate, and tryptophan, each 98% reduced in radiocarbon. Even though there is twice as much of the latter supplement in terms of absolute quantity, and each component of the latter supplement has a higher degree of radiocarbon reduction, in general the first supplement will be much more effective in reducing the radiocarbon level of histone proteins in human chromosomes because of the far greater abundance of lysine and arginine residues in histones and the greater number of carbon atoms they contribute to the chromosomes than the four amino acids in the second product.

The present invention provides methods for analyzing, labeling, reporting, and certifying the radiocarbon levels of low radiocarbon food products, particularly those food products containing proteins, hydrolyzed proteins, amino acids, nucleic acids and nucleotides or nucleosides, including relevant components of final products as well as components of lots used in manufacturing, so that manufacturers, consumers or other users of these products can have high confidence in their stated radiocarbon content. Furthermore, a method is provided to evaluate or grade low radiocarbon products in terms of their potential usefulness or effectiveness in achieving a targeted result, in particular their estimated maximal or conditional effectiveness in reducing the radiocarbon level of histones and DNA within chromosomal material (and thus the amount of genetic damage ultimately caused by radiocarbon). These effectiveness ratings make it considerably easier for consumers to choose the types and amounts of low radiocarbon food products needed to maximize possible health benefits resulting from reduction of genetic damage from radiocarbon. Furthermore, each of the steps of this process are well suited for standardization involving design control, auditing, and certification by trusted authorities or outside organizations in order establish and maintain the confidence of all consumers or users of these low radiocarbon food products. These methods may be applied to any food products intended for human or animal consumption, including vegetables and fruits, grains, meats, fish, dairy products, and nutritional supplements and additives.

For purposes of the present invention, including the description and appended claims, the following terms shall have the indicated meanings.

Amino acids: The term "amino acid(s)", when not explicitly used to denote a specific amino acid such as lysine or arginine, applies to not only free amino acids, but also to salts of amino acids and to those amino acid residues or units included within larger molecules or mixtures of molecules, including peptides, oligopeptides, polypeptides, and proteins, including hydrolyzed or partially hydrolyzed proteins. When "amino acid" is prefaced with "standard" or "primary", its meaning shall be understood to include only the twenty amino acids typically transformed into human protein.

Comprise or comprising: Throughout the entire specification, including the claims, the word "comprise" and variations of the word, such as "comprising" and "comprises," as well as "have," "having," "includes," "include" and "including," and variations thereof, means that the named steps, elements or materials to which it refers are essential, but other steps, elements or materials may be added and still form a construct with the scope of the claim or disclosure. When recited in describing the invention and in a claim, it means that the invention and what is claimed is considered to what follows and potentially more. These terms, particularly when applied to claims, are inclusive or open ended and do not exclude additional, unrecited elements or methods steps.

Consisting essentially of: In the present context, "consisting essentially of" is meant to exclude any element or combination of elements as well as any amount of any element or combination of elements that would alter the basic and novel characteristics of the invention.

DNA: The term "DNA" refers to deoxyribonucleic acid, but optionally may also be used in a general sense to include other nucleic acids such as RNA (ribonucleic acid) and to free nucleotides or nucleosides. For more details, especially pertaining to DNA and radiocarbon, see Williams, U.S. Patent Publication 2007-0104761.

Foods, food supplements, and food additives: These terms are used to describe any foods, food supplements, food additives, or any other nutritional product or component intended for use by humans of any age as well as for use by animals, including livestock and fish. Foods include such products as infant formula, liquid infusions, milk and other beverages as well as any solid or semi-solid food products. Food supplements and additives may include any vitamins or material added to any food or nutritional product. The general terms "food product" or "nutritional product" may be used to describe any such food, food supplement, food additive, or mixture thereof.

Histones: The term "histones" refers to any of the histone proteins that may be found in chromosomal material and which closely associate with DNA. For more details, especially pertaining to histones and radiocarbon, see Williams, U.S. Patent Publication 2007-0104761.

Normal or Ordinary: The terms "normal" or "ordinary", when applied to a food or a chemical substance, is used in the present disclosure and claims to mean food or chemical substances in which the radiocarbon level has not been deliberately or significantly reduced. Thus such materials contain approximately 100% of the natural background level of radiocarbon (100 pMC).

Nucleotide: The terms "nucleotide" or "nucleotides", when not clearly used to denote a specific phosphorylated nucleoside such as dCTP or guanosine-5'-monophosphate, are used as equivalent or alternative expressions for any nucleotide residue within DNA or RNA, or for the basic biochemical forms (adenosine, guanosine, cytidine, thymidine, and uridine).

Oligonucleotide: The term "oligonucleotide" as used in the present disclosure and claims refers to oligomers comprising two or more nucleotide residues, typically from 2 to about 50.

Polynucleotide: The term "polynucleotide" as used in the present disclosure and claims refers to nucleotide polymers comprising about 50 or more nucleotide residues.

Radiocarbon: The term "radiocarbon" is used in the disclosure and claims to mean carbon-14.

Radiocarbon level or concentration: For the purposes of this disclosure and claims, the terms radiocarbon level and radiocarbon concentration are used interchangeably. Reference to natural, natural abundance, background or natural background radiocarbon levels, such as "at least about 95% below natural radiocarbon levels" or "95% radiocarbon free", if not elsewhere defined, is based on assuming a current natural background level of radiocarbon of about one carbon 14 atom per every 750 billion total carbon atoms. For convenience, levels of radiocarbon may also be expressed in units of percent modern carbon (pMC), where 100% of the current natural background radiocarbon level is equal to 100 pMC. Thus the expression "about 95% below natural radiocarbon levels" illustrates about a 95% reduction in radiocarbon concentration or level, which can be expressed alternatively as "about 5 pMC." Other units for measuring radiocarbon levels, including measures of specific radioactivity and as described elsewhere in this disclosure, may also be used. This invention also allows the flexibility for reporting purposes to use any appropriate radiocarbon reference level, such as the estimated atmospheric radiocarbon level in 1950, as the baseline or natural background reference level, as long as the reference chosen is reasonable and useful, and its precise definition is readily available to the end user.

Substantially: For purposes of the present invention, unless otherwise defined with respect to a specific property, characteristic or variable, the term "substantially" as applied to any criteria, such as a property, characteristic or variable, means to meet the stated criteria in such measure such that one skilled in the art would understand that the benefit to be achieved, or the condition or property value desired is met.

In order to establish complete traceability of product lots, samples chosen from the lots, and the measured radiocarbon levels of samples, it is critical that all product lot and sample materials are adequately marked with unique identifiers. Appropriate product lot and sample identifiers may include numbers, strings containing any combination of characters or numbers, GUID's (globally unique identifiers), or any other combination of symbols or characters that can adequately identify and distinguish lots and samples. Furthermore, human readable strings or symbols printed on labels or reports may be accompanied by computer readable barcodes to permit greater accuracy and process automation. Industry standard barcode formats are generally preferred in order to facilitate general ease of use and portability. Industry standard barcodes which can be used to represent general alphanumeric identifiers include but are not limited to Code 39, Code 93, Code 128-A, and Code 128-B. Industry standard barcodes which can be used to represent general numeric-only identifiers include but are not limited to Code 11, Code 2 of 5, Interleaved 2 of 5, Plessey, MSI, and Code 128-C. These identifiers and their barcode or symbolic representations may be printed directly on product lot or sample packaging, or may be affixed using adhesive printed labels or encoded within RFID (radio frequency identification) tags. Identifiers may even consist of trace amounts of molecular tags or encoded particles mixed into the product or samples (D. C. Pregibon et al., Multifunctional Encoded Particles for High-Throughput Biomolecule Analysis, Science 315, 1393-1396 (2007)).

Using a defined and documented process appropriate to the material being measured, an adequate number of samples of sufficient size should be randomly selected from each product lot to ensure the desired accuracy and precision of radiocarbon measurements. These and other aspects of the sampling process should follow generally accepted practices and methodologies designed to minimize error and ensure reproducibility.

If it is known that the method used to grow or produce the product guarantees a uniform radiocarbon level among all biochemical components (particularly proteins, amino acids, nucleic acids and nucleotides), then a single overall radiocarbon measurement can be made on each sample, and each chemical component (such as amino acids or nucleotides) assigned this same value. Likewise, if the method of production consistently produces the same relative amount of radiocarbon reduction among the various components, then a single overall radiocarbon measurement can be made on each sample and the individual radiocarbon level of each component can be calculated using the known relative values. Otherwise, standard biochemical separation techniques should be applied to samples to extract these individual biochemical components for separate radiocarbon analyses. Although separating the samples into protein and DNA/RNA fractions prior to radiocarbon analyses may be useful and sufficient, further separation into individual amino acids and nucleotides can provide further benefit if radiocarbon levels are found to vary among these individual components. Also, if a final product lot is formed by mixing or combining known amounts of multiple intermediate lots each having components of known radiocarbon levels, then the radiocarbon levels of components in the final product can be calculated (avoiding the time, effort, and expense of additional measurement steps).

Radiocarbon measurements of sample components with precision within about 0.5% to 1% or 2% of natural background levels can be obtained using any of the standard analytical measurement techniques for radiocarbon which have been applied in the field of carbon dating. If large amounts of material are being measured and sufficient time is available, sensitive Geiger counters or other general radiation detectors such as proportional counters may be utilized, especially when used with shielded chambers and with detector arrays for coincidence detection and background elimination (Robinson, 1950; Nakhla, 1974). These may provide inexpensive, though generally less sensitive and less rapid, measurements of radiocarbon decay. Precision beta counters (typically liquid scintillation detectors) may also be employed for measuring radiocarbon decay (G. Pearson, Precise $^{14}$C measurement by liquid scintillation counting, Radiocarbon 21(1): 1-21 (1979); Verhagen, U.S. Patent Application 20060038124). However, a preferred embodiment of this invention uses AMS (accelerator mass spectrometry) to actually "count atoms," which is both faster and more sensitive than measuring radioactive decay, and is also unaffected by trace radioactive contaminants such as tritium, potassium-40, or radium. AMS methods can be used on microgram sized samples (J. S. Vogel et al., Accuracy and Precision in Dating Microgram Carbon Samples, Radiocarbon 31(2):145-149 (1989)), and have even been able to measure radiocarbon levels in DNA of selected types of human neurons (R. D. Bhardwaj et al., Neocortical neurogenesis in humans is restricted to development, PNAS 103(33): 12564-12568 (2006)). It is thus well suited for measuring the radiocarbon levels of components of a product that may be available in relatively small amounts, such as individual amino acids or nucleotides. AMS is particularly beneficial for carbon dating since it supplies accurate measurements of all carbon isotopes, including that of carbon-13, which is needed for compensating for heavy isotope dilution in fossil carbon. Although it is not critical for this application to distinguish between the stable isotopes carbon-12 and carbon-13, it can be useful for such information to still be measured and tracked for other purposes such as monitoring of source materials. Sample preparation of isolated components prior to radiocarbon analyses can vary depending on the exact method chosen, but may include combustion to carbon dioxide (see for example, A. T. Aerts-Bijma, et al., Automatic AMS Sample Combustion and $CO_2$ Collection, Radiocarbon 43(2a): 293-298 (2001)), or further reduction to pure graphite or else conversion to other suitable chemical forms such as benzene. If less precise overall measurements and longer measurement times are acceptable, inexpensive sample preparation involving simple dehydration and compression of the bulk sample into wafers or pellets for proportional counting can be used.

The measured radiocarbon levels can be reported using various units. The type of units and precision chosen can vary as long as they are useful and understandable to the intended users. It is expected that the most useful terminology for the general public will be in the form of a percentage of radiocarbon reduction from the normal natural background level, such as "95.5% radiocarbon free" or "95.5% reduction in radiocarbon". This method would use as a reference value the approximate natural background radiocarbon level for a particular year, preferably standardizing on a year (such as 1950) before which atmospheric levels of radiocarbon were significantly altered by radiocarbon from atmospheric weapons testing. Other units of radiocarbon measurements can include percent modern carbon (PMC), fraction modern carbon, parts per trillion of radiocarbon, or a measure of specific radioactivity (the number of $^{14}C$ disintegrations per unit of material per unit of time, such as dpm/g, or disintegrations per minute per gram of carbon). Radiocarbon values may also be given in ranges (ie, a radiocarbon reduction of 90-95%) or as named ranges with a predefined meaning. For example, there may be a "moderate reduction" range corresponding to 50%-75% reduction in radiocarbon, a "high reduction" corresponding to 75%-90%, a "very high reduction" corresponding to 90%-95%, and an "extremely high reduction" corresponding to 95%-100%. These levels or ranges may also be given more user-friendly or arbitrary names such as "Good", "Better", and "Best" or "Bronze", "Silver", and "Gold", as long as the actual numeric ranges are clearly defined.

FIG. 1 is a flow diagram of the product and sample labeling and analysis process used in one preferred embodiment of the present invention. The process begins with a single food, nutritional supplement or component product lot, which may be a final product lot intended for direct use by consumers, or it may be an intermediate product lot intended to be combined or mixed with other intermediate product lots before reaching the final consumer. This food product contains at least one carbon-containing chemical component, but more preferably carbon-containing chemical components comprising one or more members selected from the group consisting of (A) protein, hydrolyzed protein, or amino acids; (B) DNA, RNA, nucleotides, nucleosides, purines, pyrimidines, or other nucleic acids; and (C) mixtures of (A) and (B). In step 101, a unique product lot identifier is created for a new radiocarbon product lot. This identifier may be created using any convenient format and preferably also including a computer readable symbolic barcode. This identifier and barcode can be printed on labels which are affixed to all containers or packages holding this product lot. This product lot identifier is also entered into a computer database along with any associated relevant information about the product lot which it is desired to track. In step 102, a random sample of sufficient size for radiocarbon analysis is selected from the product lot according to a previously documented standard process. In step 103, a unique sample identifier is created for this sample. This identifier may be created using any convenient format and preferably also including a computer readable symbolic barcode. This identifier and barcode can be printed on a label which is affixed to the container or package holding the sample. This sample identifier, along with any relevant sample description, is entered into a computer database and linked to its parent product lot identifier. In step 104, the sample undergoes any physical or chemical preparation required prior to radiocarbon analysis. This analysis begins in step 105 with standard biochemical techniques to separate the sample into basic components which may include protein and DNA, or further into individual nucleotides and amino acids. The absolute or relative amounts of each of the separated components can also be quantitated. In step 106 each component is then chemically prepared using standard methods, and its radiocarbon content analyzed, preferably by AMS (accelerator mass spectrometry), the most sensitive analytical method currently available. Step 107 repeats the previous isolation and analysis steps for each additional sample component to be analyzed. Step 108 repeats steps 102 through 107 for each additional sample. A variation on the sample selection and analysis process (steps 102 through 108) is to select multiple samples but to combine two or more of them together prior to analysis. It should also be noted that the process illustrated here shows each component isolated and analyzed as separate steps, though in practice all components can be separated in a single step and their concentration and radiocarbon levels sequentially measured in a continuous process. As sample radiocarbon measurements are completed, in step 109 the data is sent to a computer system for further analysis and database storage. This analysis may include calculating the overall amounts and radiocarbon levels of each component in the product lot. In step 110, the data is used to print package labels or product inserts for use with the product lot. Alternatively, the database may be queried via remote computer access, typically involving an Internet-based query from a customer providing a product lot identifier and other information, and which returns to the customer a formatted report that may contain overall amounts of radiocarbon in each component in the product lot as well as estimated effectiveness ratings or other information or recommendations based on the specifics of the customer's product usage.

Once the amounts and radiocarbon levels of individual nucleotide and amino acid residues are known for a product lot, one or more algorithms can be used to calculate the estimated or expected effective radiocarbon reduction within newly formed chromosomal DNA and histones. Although various other terms or names may be used for this "effectiveness rating", it is essentially a measurement of the reduction of genetic damage due to radiocarbon, typically the ultimate goal for users of low radiocarbon food products.

There are two basic types of estimated or expected effectiveness ratings, "maximal effectiveness" and "conditional effectiveness". Maximal effectiveness, or maximum possible effectiveness, assumes that a sufficient amount of a low radiocarbon food product or dietary supplement is taken to meet 100% of the body's needs for those low radiocarbon nucleotides, amino acids, or other histone or DNA precursors included in the product, and that none of these low radiocarbon components are diluted by additional ingestion of foods having these same components with natural background radiation. However, any nucleotide or amino acid precursors absent from the low radiocarbon product will reduce the product's maximal effectiveness, since the body's requirements for those missing components must be met by components with natural background level in ordinary foods. Allowances can be made for a missing interconvertible amino acid, such as Phe or Tyr, since the body can readily convert one to the other as needed.

For an example of calculating maximal effectiveness, if a low radiocarbon food product contains all the required nucleotides and amino acids, each of which are 95% depleted in radiocarbon, then the supplement would have a 95% maximal effectiveness in reducing chromosomal radiocarbon. However, another low radiocarbon supplement containing nucleotides and amino acids, each of which are 95% depleted in radiocarbon, but which was missing adenosine, thymidine, lysine, and several other amino acids which all together contribute 40% of chromosomal carbons, then this supplement would have a maximal effectiveness of just 60%×95%, or 57%. Increasing the dosage or amount of the second supplement cannot increase its maximum effectiveness.

Along with every maximal effectiveness rating there should also be an approximate minimum daily dosage or amount of the low radiocarbon product needed to meet the body's nutritional needs for these components, which depends on the age and or weight of the subject. If detailed nutritional requirements for each nucleotide or amino acid are not available, minimum dosage estimates can at least be made for amino acids using daily overall protein requirements based on age or weight, and optionally with the relative amount of each amino acid based on the overall amino acid composition of the body. The minimum dosage is dependent on the amount of the one or more components present in the product in the smallest relative amount in comparison to the minimum daily recommended requirement for that component or components. For example, if 5 g of a low radiocarbon food product contains 100% of all the nucleotides and nineteen of the amino acids required for a person of a particular age and weight, but only 33% of the amount of the essential amino acid leucine required, then the minimum dosage of this low radiocarbon supplement to achieve maximal effectiveness is 15 g.

Conditional effectiveness actually applies to a specific dietary situation involving one or more low radiocarbon foods, optionally taken together with ordinary foods having natural background radiocarbon. It takes into effect the composition and amounts of each different low radiocarbon or normal food consumed, and should also ensure that overall total protein is sufficient to meet the particular protein requirement for the subject's age and weight.

This expected or estimated conditional effectiveness rating is a particularly useful value to end users in that it summarizes in a single value how beneficial the particular low radiocarbon product(s) should be in reducing chromosomal damage in a specific person under a particular set of overall dietary conditions. These algorithms take into account the amounts and levels of each of the amino acid and nucleotide components in the diet (which includes contributions both from low radiocarbon food products as well as from ordinary foods with normal levels of radiocarbon), together with the known or approximate amount of each amino acid and nucleotide typically present in human chromosomal material, to calculate the estimated effective reduction in radiocarbon for new chromosomal material being synthesized in the body. These calculations can use the overall human DNA GC (guanine/cytosine) base content of 41% and AT (adenine/thymine) base content of 59% for the overall nucleotide composition of DNA in chromatin, and data from Table 1 (taken from Table 4 in Williams, U.S. Patent Publication 2007-0104761) for the overall amino acid contribution of carbon atoms to histone proteins in chromatin.

TABLE 1

Relative overall contribution of carbon to histones of human chromatin, by amino acid, per 200 DNA base pairs

| Amino acid | Total Each Amino Acid [H1 + 2 (H2A, H2B, H3, H4)] | % Residues | Carbons per Amino Acid | Total No. Carbons | % Carbons | Cumulative % Carbons |
|---|---|---|---|---|---|---|
| Lys* (K)  | 171 | 14.3% | 6  | 1026 | 17.9% | 17.9% |
| Arg (R)   | 110 | 9.2%  | 6  | 660  | 11.5% | 29.4% |
| Leu* (L)  | 94  | 7.9%  | 6  | 564  | 9.8%  | 39.2% |
| Ala (A)   | 150 | 12.5% | 3  | 450  | 7.8%  | 47.1% |
| Val* (V)  | 78  | 6.5%  | 5  | 390  | 6.8%  | 53.9% |
| Ile* (I)  | 53  | 4.4%  | 6  | 318  | 5.5%  | 59.4% |
| Thr* (T)  | 74  | 6.2%  | 4  | 296  | 5.2%  | 64.6% |
| Glu (E)   | 56  | 4.7%  | 5  | 280  | 4.9%  | 69.5% |
| Tyr** (Y) | 31  | 2.6%  | 9  | 279  | 4.9%  | 74.3% |
| Pro (P)   | 55  | 4.6%  | 5  | 275  | 4.8%  | 79.1% |
| Ser (S)   | 75  | 6.3%  | 3  | 225  | 3.9%  | 83.0% |
| Gly (G)   | 103 | 8.6%  | 2  | 206  | 3.6%  | 86.6% |
| Gln (Q)   | 38  | 3.2%  | 5  | 190  | 3.3%  | 89.9% |
| Phe** (F) | 19  | 1.6%  | 9  | 171  | 3.0%  | 92.9% |
| His* (H)  | 22  | 1.8%  | 6  | 132  | 2.3%  | 95.2% |
| Asn (N)   | 28  | 2.3%  | 4  | 112  | 2.0%  | 97.2% |
| Asp (D)   | 25  | 2.1%  | 4  | 100  | 1.7%  | 98.9% |
| Met** (M) | 10  | 0.8%  | 5  | 50   | 0.9%  | 99.8% |
| Cys** (C) | 4   | 0.3%  | 3  | 12   | 0.2%  | 100.0% |
| Trp* (W)  | 0   | 0.0%  | 11 | 0    | 0.0%  | 100.0% |
| TOTAL | 1196 amino acids | | | 5736 carbon atoms | | |

*Essential amino acid
**Essential but interconvertible (Phe/Tyr, Met/Cys)

Should further investigation or experiments show that the overall human histone amino acid composition significantly differs from the composition estimated and shown in Table 1 or elsewhere in this invention, this table listing the relative carbon contribution of each amino acid to histones can be revised to incorporate this updated or more accurate information, and this revised histone composition can be used to re-estimate the optimal low radiocarbon amino acid compositions needed to maximize reduction of radiocarbon and histones or to perform other calculations as described in this invention. Likewise, revisions to DNA GC and AT content, or to the relative amount of DNA and histones, can also be handled by appropriate adjustments to the tables and calculations used in this invention.

Algorithms used for calculating the expected effective radiocarbon reduction or reduction of genetic damage due to radiocarbon may include the use of one or more relative response factors (RRF's) for each individual chemical component. These relative response factors can be used to reflect the absorption, uptake, or other physiological issues which might influence the net amount of each component which ultimately becomes incorporated into chromosomal material, or that relate to the genetic importance of each component within the chromosomal material, or that give proper weight to those components which have the greatest impact on birth defects, aging, cancer, or genetic diseases. For example, relative response factors for essential amino acids may be higher than relative response factors for non-essential amino acids since the latter face additional competition for incorporation into histones from other amino acid units produced within the body. Relative response factors for nucleic acids, because of their actual incorporation within DNA, may be higher than that of amino acids which only become incorporated into the surrounding histones. Relative response factors for guanosine and cytidine nucleotides may be higher than those for adenosine and thymidine because of the tendency of gene-coding regions to be located in the GC-rich portions of the DNA. Relative response factors for amino acids present in larger amounts as free amino acids may be higher than for other amino acids only present in polypeptide form and which require proteolysis before they can be absorbed. Also, each component may have multiple relative response factors, for example one which is concentration independent and another which varies depending on the amount of the component which is present. These relative response factors may be determined based on theoretical estimates (using data such as known GC and AT abundances in human DNA or on the relative number of carbon atoms each type of amino acid contributes to histones), on experimental studies performed using various combinations and amounts of low radiocarbon nucleic acids and amino acids on microorganisms, animals, or human volunteer subjects, or on a combination of both theory and experiment. Such methods and the calculation of RRFs are known to a person skilled in the art, although their application to nutritional supplements has not previously been described.

FIG. 2 illustrates a calculation spreadsheet used to estimate the effective percentage of carbons each nucleotide and amino acid contributes to human chromosomal material. This data can be used in calculating either maximal or conditional effectiveness. The data used in this example are based on the assumptions that overall human DNA GC base content is 41% and AT base content is 59%, that overall chromosomal content is similar to that of a typical nucleosome having 200 DNA base pairs associated with nine histone protein molecules—one H1 and two each of H2A, H2B, H3, and H4 (Williams, U.S. Patent Publication 2007-0104761). While the underlying method would remain unchanged, a revised version of this table can be made should further research indicate that any of these assumptions should be modified. Column A lists the individual DNA nucleotide and histone amino acid components. Column B contains the total number of each nucleotide or amino acid residue per nucleosome unit. Column C contains the number of carbon atoms found in each type of nucleotide or amino acid residue. Column D contains the product of the values found in B and C, which equals the total number of carbon atoms contributed by each type of nucleotide or amino acid to a nucleosome unit. Assuming that the chromosome overall has the same relative composition as the nucleosome, D thus contains the relative number of carbon atoms contributed to chromosomal material by each of the components. Column E contains a Relative Response Factor (RRF) which can be different for each component if desired, and which is used to reflect the relative significance of a radiocarbon decay in that material in terms of genetic damage. In this example, for the purpose of illustration, the nucleotides adenosine and thymidine are each given the baseline RRF of 1.0, whereas guanosine and cytidine, which are slightly more prevalent in coding regions of DNA and thus presumably more vital to DNA function, are each given a slightly higher RRF of 1.1. On the other hand, all amino acids in this example are given a lower RRF of 0.60 to indicate that radiocarbon decay in histone proteins is estimated to be only 60% as damaging as that to DNA adenosine and thymidine residues. Actual RRF values may be based on the best theoretical or experimental data available at the time, and may possibly also differ when used to estimate different types of health risks from radiocarbon damage to chromosomes, such as cancer, birth defects, or aging. Column F contains the Effective (relative) Number of Carbons, and is simply the product of Columns D and E. Finally, Column G contains the Effective Percentage of Carbons within chromosomes for each type of DNA and histone residue, and is simply the corresponding value in F divided by the sum of all the values in column F, which in this example has a sum equal to 7515.4. These values for Effective Percentage of Carbons within chromosomes for each nucleotide and amino acid component indicate the maximum benefit each particular component of a low radiocarbon diet will have on new chromosomal material being built using these components. These percentages are then used when calculating the overall expected effective radiocarbon reduction (or reduction of genetic damage) in new chromosomal material due to a particular low carbon diet. This is further illustrated in the next figure.

FIG. 3 illustrates a calculation spreadsheet used to determine the estimated effective percentage of radiocarbon reduction in new chromosomal material (i.e., conditional effectiveness) provided by a low radiocarbon food product which is also eaten in conjunction with ordinary food having natural background levels of radiocarbon. Column A lists the individual DNA nucleotide and amino acid components. Column B contains the Effective Percentage of Carbons in the Chromosome for each component, as calculated previously in FIG. 2 (Column G). Column C contains the known, measured, or estimated reduction in the radiocarbon level of each component in the low radiocarbon food. Column D contains the actual amount (mass) of each type of component in the low radiocarbon food. Column E similarly contains the actual amount (mass) of each type of component in the normal food containing natural background level of radiocarbon (and a 0% level of radiocarbon reduction). Column F is the total amount of each component in all food eaten, and is simply the amount of low radiocarbon food in Column D added to the amount of normal food in Column E. Columns D, E, and F can use any appropriate measurement of mass or weight as long as they all three use the same unit. Also, for the purpose of this invention, only nucleotide and amino acids portions of low radiocarbon and normal food are of interest; fats, sugars, and other components are ignored. Column G is the amount of low radiocarbon food as a percentage of the total food, and is simply the value in Column D divided by the value in Column F. Column H contains the overall effective radiocarbon reduction in the chromosome for each component. The sum of the values in Column H is the net overall effective radiocarbon reduction in the chromosome for all nucleotide and amino acid components together. This is the value most useful or of most interest to the consumer to indicate how effective a particular low radiocarbon food product will be in reducing radiocarbon levels in new chromosomal material when taken with the stated amount of ordinary food. Thus, in this embodiment, the estimated overall effective radiocarbon reduction for 7.88 g of nucleotides and amino acids in this low radiocarbon food product taken together with 4.01 g of these components in normal food is 72.23%.

One skilled in the art can readily make numerous variations of these embodiments, including simplified estimates of radiocarbon reduction when all DNA or histone protein precursors have the same levels of radiocarbon reduction and response factors, or more complicated estimates involving several different low radiocarbon and normal foods all having components with differing radiocarbon levels, or which involve multiple RRF's for each component.

Most if not all radiocarbon reduction within chromosomal materials likely occurs primarily during growth of new cells, and this varies according to the individual's stage in life. If the subject's age, weight and sex are available, additional estimates of chromosomal radiocarbon reduction obtained or obtainable over an extended or arbitrary time with a particular low radiocarbon diet can be made using growth charts (Williams, U.S. Patent Publication 2007-0104761).

Results of radiocarbon analyses may be provided to consumers or users of the product using labels printed on or attached to the product, or by package inserts, or by interactive electronic reporting means involving remote computer access, particularly via the Internet or a VPN (virtual private network). These labels or reports may include any relevant information pertaining to the radiocarbon analyses, including overall radiocarbon levels and amounts of material, radiocarbon levels and amounts of individual components (nucleic acids, nucleotides, protein, amino acids, etc.), recommended serving sizes or dosages, recommendations of additional complementary low radiocarbon products or other general nutritional products, and estimates of expected reduction of radiocarbon in chromosomal materials or of expected reduction in chromosomal damage events. These labels may further include mechanisms to minimize fraud and counterfeiting. Such anti-fraud mechanisms may include allowing end users online access to a central low radiocarbon certification authority to use a unique barcode on the package to look up details related to that particular package or product lot, including time and date packaged, location(s) where it was sold, and other manufacturer or package details. Labels or associated packaging can also employ difficult-to-forge seals, complex printing, holograms, RFID tags, or similar fraud prevention devices.

FIG. 4 illustrates a sample product label of one preferred embodiment. Item 401 is the computer readable product lot identifier barcode, in this instance using Code 128-B format and including human-readable text immediately below. Item 402 is the product name. Item 403 is the product lot number, and item 404 is the product identifier. In this example the complete product lot identifier encoded in the barcode includes both the product id and the lot number. Item 405 is a table listing all the relevant chemical components within this product that have a direct impact on chromosomal material, their amounts, and their radiocarbon levels. Item 406 provides values for the estimated overall effectiveness of this product in reducing chromosomal radiocarbon for two particular product usage situations. Item 407 directs the user to an Internet location where additional useful product information may be obtained.

Interactive electronic reporting of results using the Internet, a VPN, or other electronic networks may also be done in a wide variety of mechanisms. However, one element common to all these mechanisms is that the user must provide a product lot identifier. Additional optional information which may be queried can include customer specific details such as weight, age or birth date, sex, type of diet, dietary preferences, or relevant health issues. These customer specific details should preferably remain anonymous in order to protect the privacy rights of the customer, but for convenience may optionally be persisted on either the client's machine or the Internet server using standard mechanisms such as customer profiles or cookies.

Figure 5:
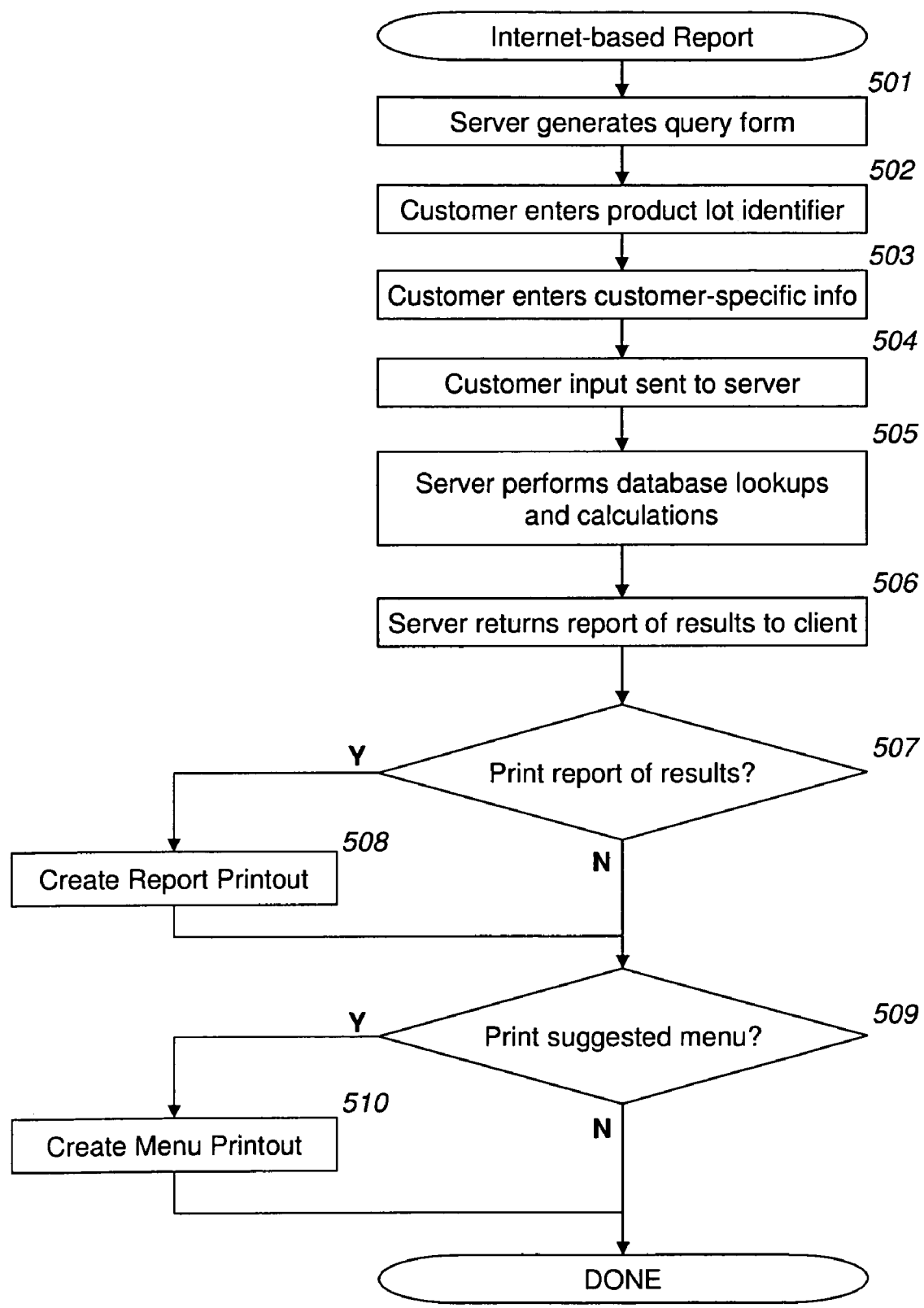
FIG. 5 is a flow diagram of a remote computer access reporting process used in another embodiment of the present invention.

FIG. 5 is a flow diagram of one preferred embodiment which includes detailed reporting of product information over the Internet. In step 501 the user or customer connects to the appropriate web site URL (Uniform Resource Locator), and the web server responds by providing the user with a query form containing one or more data input fields. In step 502 the user enters in the unique identifier or barcode for the product lot of the particular low radiocarbon product they are interested in. In step 503 the user may optionally enter additional information about the intended consumer, such as birth date or age, weight, sex, the amount of the low radiocarbon product being consumed, types and amounts of other normal food being eaten, dietary preferences, or similar personal information. This personal information is preferably anonymous to protect user privacy, but for convenience may be stored or persisted on either the server or client PC using standard means which may include user profiles or cookies. After entering all requested data, in step 504 the user submits this data back to the server. In step 505 the server performs any necessary database lookups of product information or user profile settings, and uses this information to calculate amounts and radiocarbon levels of various product components such as amino acids and nucleotides, as well as the estimated effectiveness of the product in reducing radiocarbon incorporation into the chromosomal material of the consumer based on the data previously provided by the user. In step 506 the server formats and returns the results in a user-friendly report format which may also include additional explanatory material or hyperlinks to additional information or alternative reports. In step 507 the user is offered an opportunity to create a report printout (508). In step 509 the user is offered an opportunity to create a dietary menu (510) listing suggested types and amounts of various low radiocarbon food items which may be appropriate for the consumer in achieving a desired level of chromosomal radiocarbon reduction.

Internet or other interactive reporting mechanisms may facilitate "what if" scenarios where the user can enter the type and amount of any number of different normal and low radiocarbon food products consumed over various periods of time to estimate the overall effectiveness in reducing radiocarbon incorporation into chromosomal material or in reducing genetic damage events.

Interactive reporting mechanisms may also provide recommendations of other low radiocarbon or even normal radiocarbon food products or supplements which may be useful in maximizing radiocarbon reduction of chromosomal material or in providing any other health benefit. For example, a consumer may enter personal information such as age and weight together with the types and amounts of a number of low radiocarbon and normal food products intended to be eaten over a given period of time. If the combination of food products shows that the normal food contains considerable lysine, it may recommend additional supplementation with low radiocarbon lysine, within safe limits. Also, if the foods listed by the consumer are low in a particular vitamin or mineral, it may recommend the appropriate vitamin or mineral supplements, even though these have no direct impact on radiocarbon reduction of chromosomal material.

Figure 6:
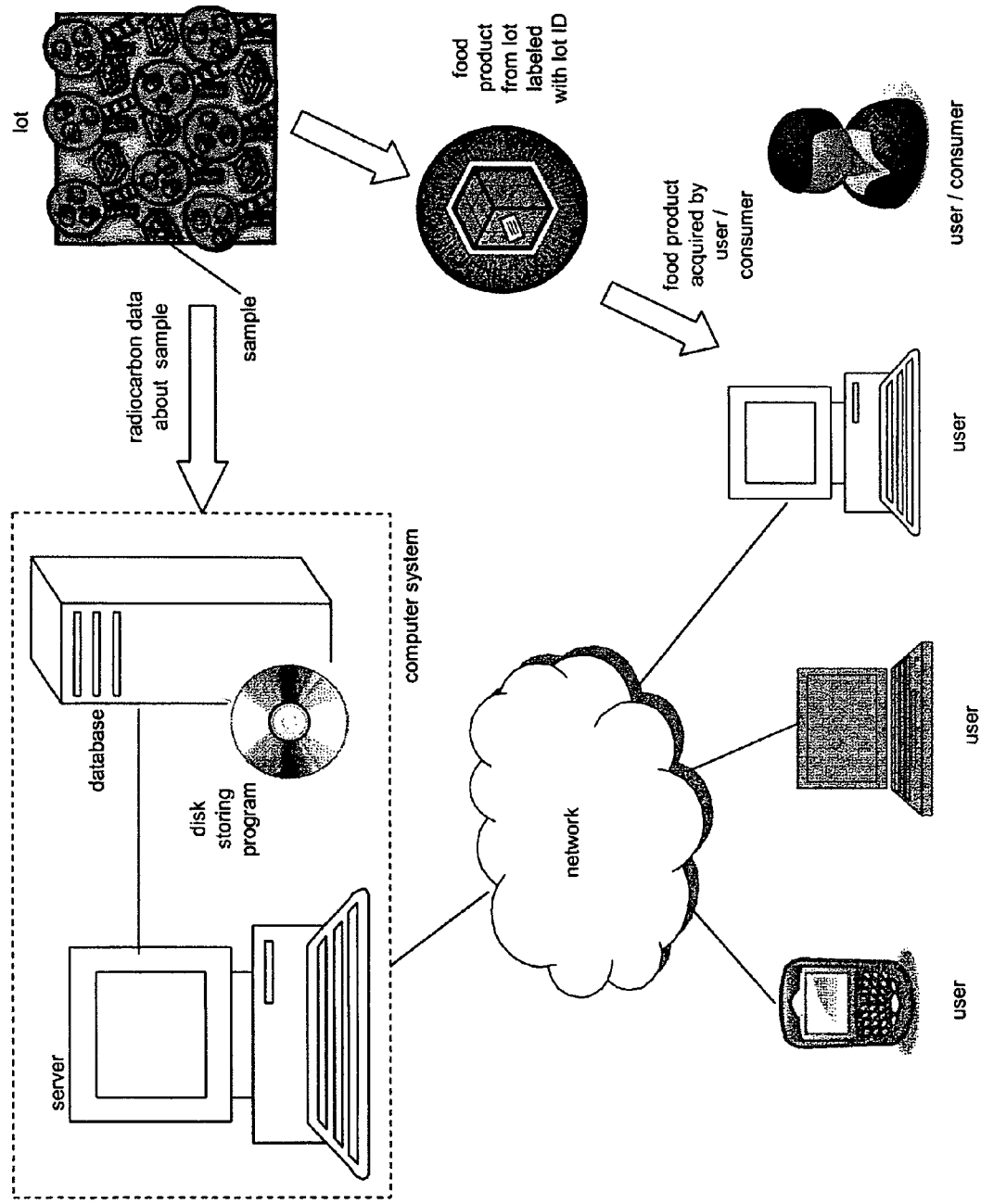
FIG. 6 illustrates operation of an embodiment of the invention utilizing remote access by a user of a computer database comprising stored product information.

FIG. 6 illustrates operation of an embodiment of the invention utilizing remote access by a user of a computer database comprising stored product information, for example, as described and discussed above. For example, including in FIG. 6 is a computer system comprising a server, database and disk storage medium, on which data and information about samples and products can be stored. Such information can also be included on products, including intermediate products used to make final products for sale to the consumer; information can include identification information in computer readable form. A user, including multiple users, can access the computer system using alternative devices, including telephones, cell phones, personal digital assistants, as well as laptop and desktop computers. Suitable access can be acquired via telephone, cable, fiber and other systems known in the art, including in particular, the world wide web or internet.

Additional relevant standard product analyses and certification steps not related to radiocarbon may also be done in conjunction with this method. For example, a food product may be certified both in terms of overall radiocarbon content, protein radiocarbon content and nucleic acid radiocarbon content, and may also have a standard "Nutritional Facts" analysis of fat, carbohydrate, protein, vitamins, and minerals which is independent of radiocarbon. This additional information may be provided on a separate label or may be combined on a single label together with radiocarbon-related information.

Furthermore, the processes of labeling and tracking low radiocarbon product lots and samples as described here can be further integrated in a more comprehensive tracking system, such as ones that monitor agricultural or livestock products from planting or birth and on through harvesting or slaughter, processing, and packaging (Montanari et al., U.S. Pat. No. 5,478,990; Beck et al., U.S. Pat. No. 7,085,777).

Industry standards and quality systems regulations such as ISO 9000 (from the International Organization for Standardization, www.iso.org), GMP (Good Manufacturing Practices, http://www.fda.gov/cdrh/devadvice/32.html), or from GAMP (Good Automated Manufacturing Practice, www.ispe.org/gamp) may be adopted in whole or in part in creating and implementing a particular certified process according to this invention. Particular aspects of this invention which can be implemented in coordination with trusted and qualified outside organizations include:

Design or approval of the processes used in product and sample handling, labeling, and tracking.

Design or approval of the processes related to the chemical processing or separation techniques employed.

Design or approval of the processes related to the calibration, maintenance and operation of analytical instruments.

Design or approval of the computer data system, including its implementation, reliability, accuracy, performance, scalability, backup and security, with particular attention to means of preventing tampering or other deliberate or accidental altering or loss of data.

Design or approval of the reporting system or labeling used (accurate as well as clear and understandable to end users).

Design or approval of training materials and training programs for personnel performing any of these processes.

Design or approval of troubleshooting, error correction and avoidance, and risk management processes.

Design or approval of documentation control and change control processes.

Ongoing random sampling, monitoring or auditing by outside agencies or organizations to ensure continued compliance.

A preferred embodiment of this invention involves using AMS for measuring the radiocarbon levels of individual amino acid and nucleotide components in samples taken from a low radiocarbon food product according to the process shown in FIG. 1, then applying an algorithm for estimating the effectiveness of a low radiocarbon product as illustrated in FIG. 2 and FIG. 3, then applying a product label similar to that illustrated in FIG. 4 to the product package, furthermore employing a qualified outside organization to certify the design, documentation and implementation of each of the essential processes or steps involved.

Additional modifications within the spirit of the invention will be apparent to those skilled in the art. For example, low radiocarbon products containing essentially only protein may receive a radiocarbon reduction effectiveness rating which only pertains to the estimated amount of radiocarbon reduction within histones and which ignores any impact on DNA. As another example, the graphic format or layout or fonts, the type of barcode or barcodes, and the selection and ordering of individual components which appear on the labels or reports may be altered as necessary to satisfy business or regulatory requirements. A further embodiment includes product information, marketing, advertising, or direct product ordering links on an Internet reporting form.

Another embodiment is directed to a computer-implemented method for providing personalized food radiocarbon information for a consumer of a food product, the food product having associated therewith product identification (ID) information and lot ID information corresponding to a lot from which the food product originated, the method comprising: (a) inputting to a computer system: (i) the product ID information and lot ID information from a food product which the user has acquired; and (ii) personal consumer information comprising one or more personal characteristics of the consumer of the food product; and (b) the computer system calculating personalized food radiocarbon information for the consumer based on the inputted product ID information, lot ID information and personal consumer information and based on preexisting radiocarbon information associated with the lot ID information of the food product.

A further embodiment is directed to a computer-readable medium for storing instructions for causing a computer to perform a method for providing personalized food radiocarbon information for a consumer of a food product, the food product having associated therewith product lot ID information corresponding to a lot from which the food product originated, the instructions causing the computer to: (a) provide an interface to allow user input of: (i) the product lot ID information of a food product which the user has acquired; and (ii) personal consumer information comprising one or more personal characteristics of the consumer of the food product; and (b) calculate personalized food radiocarbon information for the consumer based on the inputted lot ID information and personal consumer information and based on preexisting radiocarbon information associated with the lot ID information of the food product.

In another embodiment is directed to a method for providing personalized food radiocarbon information for a consumer of a food product, comprising: (a) providing a plurality of lots of food products; (b) determining radiocarbon information about samples of food products from the lots; (c) associating the radiocarbon content of the samples from each lot with a lot ID; (d) labeling food products with the lot ID corresponding to the lot from which the food product originates; (e) providing a computer system for: (i) allowing user input of the lot ID of a food product the user has acquired and personal consumer information comprising one or more personal characteristics of the consumer of the food product; and (ii) calculating personalized food radiocarbon information for the consumer based on the personal consumer information and the radiocarbon content associated with the lot ID of the food product.

Any range of numbers recited in the specification hereinabove or in the paragraphs and claims hereinafter, referring to various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. Furthermore, the term "about" when used as a modifier for, or in conjunction with, a variable, characteristic or condition is intended to convey that the numbers, ranges, characteristics and conditions disclosed herein are flexible and that practice of the present invention by those skilled in the art using temperatures, concentrations, amounts, contents, carbon numbers and properties that are outside of the range or different from a single value, will achieve the desired result, methods, particularly computer-implemented methods, for analyzing, labeling, reporting, and certifying the radiocarbon abundance levels of low radiocarbon food products, including relevant chemical components of final products as well as components of lots used in manufacturing, so that manufacturers, consumers or other users of these products can have high confidence in their stated radiocarbon content and a better understanding of their potential effectiveness in reducing genetic damage.

All documents described herein are incorporated by reference herein, including any priority documents and/or analytical procedures. The principles, preferred embodiments, and modes of operation of the present invention have been described in the foregoing specification. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

References Cited

U.S. Patent Documents:

| Document No. | Published | Inventor |
|---|---|---|
| U.S. Pat. No. 5,471,785 | December 1995 | Matthews |
| U.S. Pat. No. 5,478,990 | December 1995 | Montanari et al. |
| U.S. Pat. No. 5,956,896 | September 1999 | Miekka et al. |
| U.S. Pat. No. 7,085,777 | August 2006 | Beck et al. |
| U.S. Appl. 20070104761 | January 2006 | Williams |
| PCT Appl. PCT/US07/10775 | November 2008 | Williams |
| U.S. Appl. 20060038124 | February 2006 | Verhagen |

Non-Patent Literature Documents:

R. D. Bhardwaj, et al., *Neocortical neurogenesis in humans is restricted to development*, PNAS 103(33): 12564-12568 (2006).

A. T. Aerts-Bijma, et al., *Automatic AMS Sample Combustion and $CO_2$ Collection*, Radiocarbon 43(2a): 293-298 (2001).

S. M. Nakhla et al., *Cairo Natural Radiocarbon Measurements I*, Radiocarbon 16(1): 1-5 (1974)

G. Pearson, *Precise $^{14}C$ measurement by liquid scintillation counting*, Radiocarbon 21(1): 1-21 (1979).

D. C. Pregibon, et al., *Multifunctional Encoded Particles for High-Throughput Biomolecule Analysis*, Science 315, 1393-1396 (2007).

J. S. Vogel, et al., *Accuracy and Precision in Dating Microgram Carbon Samples*, Radiocarbon 31(2):145-149 (1989).

The invention claimed is:

1. A computer-implemented method for providing personalized food radiocarbon information for a consumer of a food product, the food product having associated therewith product lot identification (ID) information corresponding to a lot from which the food product originated, the method comprising:
    (a) inputting to a computer system:
        (i) the lot ID information from a food product which the user has acquired; and
        (ii) personal consumer information comprising one or more personal characteristics of the consumer of the food product; and
    (b) the computer system calculating personalized food radiocarbon information for the consumer based on the inputted lot ID information and personal consumer information and based on preexisting radiocarbon information associated with the lot ID information of the food product; and
    (c) delivering to the consumer the information calculated in step (b).

2. The method of claim 1, wherein the preexisting radiocarbon information is previously stored in computer memory or a database accessible by the computer system.

3. The method of claim 1, wherein the computer system is located remotely from the user and the inputting step (a) is done via a local user computer.

4. The method of claim 3, wherein the local user computer communicates with the computer system via the Internet.

5. The method of claim 3, wherein the personalized food radiocarbon information is provided to the user on a display on the local user computer.

6. The method of claim 1, further comprising calculating the personalized food radiocarbon information based on (a) data entered about the consumer's diet and/or eating habits and (b) specific data indicative of the radiocarbon content of samples from the lot of the food product.

7. The method of claim 1, wherein the personal characteristics include one or more of age, weight, sex and dietary information.

8. The method of claim 7, wherein the personalized food radiocarbon information includes recommending additional food products to the consumer based on one or more of the personal characteristics to achieve a reduction in the incorporation of radiocarbon in newly formed chromosomal DNA and histones.

9. The method of claim 1, wherein the personalized food radiocarbon information comprises information about the effective radiocarbon reduction within newly formed chromosomal DNA and histones.

10. The method of claim 1, wherein the personalized food radiocarbon information comprises information about the reduction of genetic damage due to the radiocarbon content in the food product.

* * * * *